United States Patent [19]

Schrock et al.

[11] Patent Number: 5,089,592
[45] Date of Patent: Feb. 18, 1992

[54] BISCYCLOBUTARENE MONOMER COMPRISING TWO CYCLOBUTARENE MOIETIES BRIDGED BY A DIVALENT RADICAL COMPRISING AT LEAST ONE BENZOTHIAZOLE OR BENZIMIDAZOLE LINKAGE

[75] Inventors: Alan K. Schrock, Lake Jackson, Tex.; William J. Harris; Norman L. Madison, both of Midland, Mich.

[73] Assignee: The Dow Chemical Company, Midland, Mich.

[21] Appl. No.: 355,767

[22] Filed: May 25, 1989

Related U.S. Application Data

[63] Continuation-in-part of Ser. No. 205,141, Jun. 9, 1988, Pat. No. 4,864,010.

[51] Int. Cl.$^5$ .................... C08F 38/00; C08F 132/08; C08G 63/00
[52] U.S. Cl. .................... 528/185; 528/176; 528/183; 548/217; 548/577
[58] Field of Search .................... 528/176, 183, 185; 548/217, 577

[56] References Cited

U.S. PATENT DOCUMENTS

| | | | |
|---|---|---|---|
| 3,257,204 | 6/1966 | Sus et al. | 424/272 |
| 3,586,670 | 6/1971 | Brenneisen et al. | 260/240 |
| 3,669,979 | 6/1972 | Freyermuth | 260/304 |
| 3,822,356 | 7/1974 | Brenneisen et al. | 424/272 |
| 4,051,108 | 9/1977 | Heiminiak et al. | 260/47 |
| 4,108,835 | 8/1978 | Arnold et al. | 528/183 |
| 4,229,566 | 10/1980 | Evers et al. | 528/185 |
| 4,351,882 | 9/1982 | Concannon et al. | 428/422 |
| 4,359,567 | 11/1982 | Evers | 528/179 |
| 4,505,842 | 3/1985 | Kurkov et al. | 252/500 |
| 4,522,745 | 6/1985 | Kurkov | 252/500 |
| 4,578,432 | 3/1986 | Tsai et al. | 528/183 |
| 4,687,823 | 8/1987 | Kirchhoff et al. | 526/284 |
| 4,835,246 | 5/1989 | Tsai et al. | 528/337 |
| 4,900,806 | 2/1990 | Arnold et al. | 528/337 |
| 4,977,223 | 12/1990 | Arnold et al. | 525/432 |

FOREIGN PATENT DOCUMENTS 016889 1/1985 Japan .

OTHER PUBLICATIONS

"Polybenzazoles" by Yoshio Imai, Keikichi Uno & Yoshio Iwakura; pp. 179–187, *Encyclopedia of Polymer Science & Engineering* vol. 11.

"Synthesis and Properties of High Strength High Modules ABA Block Copolymers" by Tsu T. Tsai and Fred E. Arnold; *Journal of Polymer Science*: Part A: Polymer Chemistry, vol. 27, 2839–2848 (1989).

*Hawley's Condensed Chemical Dictionary*, 11th Edition.

"The Birth Of Ordered Polymer, Technology For Air Force Applications" by Fred E. Arnold Mat. Res. Soc. Symp Proc. vol. 134–1989 Materials Research Society-pp. 75–82.

"Structural Modification of Rigid-Rod Polymers" by Fred E. Arnold Mat. Res. Soc. Symp Proc. vol. 134–1989 Materials Research Society-pp. 117–126.

"Synthesis & Dilute Solution Characterization of Extended Chain Poly(benzazoles)" by Andrea W. Chow, et al. Mat. Res. Soc. Symp Proc. vol. 134–1989 Materials Research Society pp. 173–177.

"An Integrated Laboratory Process For Preparing Rigid Rod Fibers From the Monomers" by Harvey D. Ledbetter et al.; Mat. Res. Soc. Symp Proc. vol. 134–1989 Materials Research Society-pp. 253–264.

"Thermal Stability of Rigid-Rod Polymers" by Lisa R. Denny et al.; Mat. Res. Soc. Symp Proc. vol. 134–1989 Materials Research Society-pp. 117–126.

*Primary Examiner*—Harold D. Anderson
*Assistant Examiner*—T. Mosley
*Attorney, Agent, or Firm*—Charles J. Enright

[57] ABSTRACT

A biscyclobutarene monomer is prepared comprising two cyclobutarene moieties bridged by a divalent radical having at least one benzoxazole, benzothiazole or benzimidazole linkage. A reactive biscyclobutarene oligomer is also prepared by reacting a cyclobutarene-carboxylic acid, a diaminodihydroxyarene, diaminodithiolarene or tetraaminoarene and either an aromatic diacid or an aromatic diacid chloride. the monomers and reactive oligomers can be polymerized to form polymers exhibiting outstanding thermooxidative stability at high temperatures for prolonged time periods.

7 Claims, 4 Drawing Sheets

BISCYCLOBUTARENE MONOMER COMPRISING TWO CYCLOBUTARENE MOIETIES BRIDGED BY A DIVALENT RADICAL COMPRISING AT LEAST ONE BENZOTHIAZOLE OR BENZIMIDAZOLE LINKAGE

The U.S. Government has a paid-up license in this invention and the right in limited circumstances to require the patent owner to license others on reasonable terms as provided for by the terms of Contract No. F33615-85-C-5092 awarded by Wright-Patterson Air Force Base.

CROSS-REFERENCE TO RELATED APPLICATION

This is a continuation-in-part of copending U.S. application Ser. No. 205,141, filed June 9, 1988, which has now issued as U.S. Pat. No. 4,864,010.

BACKGROUND OF THE INVENTION

This invention relates to monomers and oligomers of biscyclobutarenes and polymers derived therefrom. More specifically, it relates to monomers, oligomers, and polymers of biscyclobutarenes that are bridged by at least one benzoxazole, benzothiazole, or benzimidazole linkage.

Polymers derived from biscyclobutarene monomers are disclosed in U.S. Pat. No. 4,540,763. The polymers are prepared by subjecting biscyclobutarene monomers to temperatures sufficient for polymerization. The polymers exhibit excellent thermal stability at high temperatures, good chemical resistance to most industrial solvents, good physical and mechanical properties, and low sensitivity to water. The polymers are useful for preparing composites, coatings and films; and as adhesives.

Although the polymers of U.S. Pat. No. 4,540,763 exhibit excellent thermal stability at high temperatures, numerous applications in high performance industries, such as the aerospace industry, require polymers for advanced composites that not only exhibit high temperature thermal stability but also exhibit high temperature thermal stability in air for prolonged time periods. Unfortunately, many of the polymers of U.S. Pat. No. 4,540,763 do not exhibit the long term thermooxidative stability required for high performance applications. The polyvalent organic and inorganic bridging groups of the biscyclobutarenes are susceptible to oxidation reactions when subjected to elevated temperatures for extended times. Particularly susceptible are aliphatic bridging groups.

In view of the deficiencies of the prior art, it would be desirable to prepare polymers derived from biscyclobutarene monomers and oligomers that exhibit outstanding thermooxidative stability for prolonged time periods.

SUMMARY OF THE INVENTION

In one aspect, the invention is a biscyclobutarene monomer and a biscyclobutarene oligomer derived therefrom. The biscyclobutarene monomer comprises two cyclobutarene moieties bridged by a divalent radical having at least one benzoxazole, benzothiazole, or benzimidazole linkage. The biscyclobutarene oligomer comprises the reaction product of a cyclobutarene-carboxylic acid, either a diaminodihydroxyarene, diaminodithiolarene, or tetraaminoarene, and either an aromatic diacid or an aromatic diacid chloride.

In another aspect, the invention comprises a process for preparing a polymer from the biscyclobutarene monomer or the biscyclobutarene oligomer of this invention. The process comprises the step of subjecting the monomer or oligomer to ring scission polymerization conditions.

The polymers derived from the biscyclobutarene monomers and the biscyclobutarene oligomers exhibit excellent thermooxidative stability at high temperatures for prolonged time periods. The benzoxazole, benzothiazole and benzimidazole linkage of the divalent radical contributes to the thermooxidative stability of the bridging member, and therefore the thermooxidative stability of the polymer is enhanced. The polymers are useful as matrix resins for advanced composites and as high performance adhesives for bonding substrates. They are also useful for any other application requiring service in a harsh environment.

DETAILED DESCRIPTION OF THE INVENTION

For purposes of describing this invention, a cyclobutarene is a substituted or unsubstituted aromatic compound to which is fused one or more cyclobutane rings or one or more substituted cyclobutane rings. The aromatic ring of the cyclobutarene can be substituted with nitro, chloro, bromo, or any other group that will not adversely affect the thermooxidative stability of the polymers derived from the monomers of this invention. Likewise, the cyclobutane ring can be substituted with similar thermooxidatively stable groups. The most preferred cyclobutarene is benzocyclobutene.

The monomers of this invention are biscyclobutarene monomers. The cyclobutarene moieties of the monomer are bridged by a divalent radical that has at lest one benzoxazole, benzothiazole or benzimidazole linkage. Processes for preparing benzoxazole, benzothiazole or benzimidazole linkages within the scope of this invention are described in U.S. Pat. No. 4,533,693, which is incorporated by reference herein. Preferably, the benzoxazole, benzothiazole or benzimidazole linkage is a bis(benzoxazole, benzothiazole or benzimidazole) linkage corresponding to the following general formula:

wherein $Z=O$, $S$, $NR'$; $R'=$hydrogen, aromatic, or aliphatic moiety; and Ar is any aromatic ring or ring system. It is understood that Ar may be heterocyclic but more preferably is carboxylic and more preferably is hydrocarbyl. It is also understood that each Ar may comprise a single aromatic ring, a fused ring system, or an unfused ring system containing two or more aromatic moieties joined by direct divalent bonds or by one or more divalent moieties, $R^1$. More preferably, the benzoxazole, benzothiazole or benzimidazole linkage corresponds to one of the following formulae:

wherein Z is an oxygen or sulfur atom or a group wherein R' is hydrogen or a monovalent aliphatic or aromatic radical;

R is methyl, halo, phenyl, or phenyloxy;

R¹ is a direct bond, arylene, oxygen, carbonyl, sulfur, sulfinyl, or sulfonyl;

m is zero, 1 or 2; and n is zero, 1, 2 or 3.

As the term is used herein, "arylene" refers to a divalent aromatic group. Preferred arylene is phenylene.

The most preferred benzoxazole linkage has the following formula:

A preferred monomer with the most preferred benzoxazole linkage is a bisbenzocyclobutene monomer of the formula:

The preferred monomers can be prepared by the condensation reaction of a cyclobutarene-carboxylic acid and a diaminodihydroxyarene, diaminodithiolarene or tetraaminoarene in which each hydroxy, thio, or amine group is ortho to an amine group at elevated temperatures. A cyclobutarene-carboxylic acid is defined as a cyclobutarene substituted with carboxyl, as, for example, benzocyclobutene-4-carboxylic acid. The reaction requires a reactive reagent that acts as a dehydrating solvent for the condensation reaction and solubilizes the prepared monomer. One well known reactive reagent is polyphosphoric acid. A more preferred reagent, disclosed in Ueda et al., *J. Polymer Sci.*: Part A: Polymer Chem., 24, 1019, (1986), is a mixture of methanesulfonic acid and phosphorus pentoxide. The process conditions disclosed in Ueda for preparing polybenzoxazole polymers are generally suitable for preparing the monomers of this invention.

As an example of the monomer preparation, the monomer of formula 1 can be prepared by reacting 2 moles of benzocyclobutene-4-carboxylic acid with 1 mole of 1,3-diamino-4,6-dihydroxybenzene in the presence of a sufficient quantity of about 10 weight percent phosphorus pentoxide in methanesulfonic acid. Enough phosphorus pentoxide should be present so that the water of condensation is calculated to consume no more than about 15 weight percent of the phosphorus pentoxide present at the start of the condensation reaction. The reaction mixture is stirred under nitrogen at about 100° C. for about three hours and then cooled to room temperature. The monomer can be precipitated from the mixture by contact with cold water and can be collected by filtration.

In another embodiment of this invention, reactive biscyclobutarene oligomers are prepared by reacting a cyclobutarene-carboxylic acid, a diaminodihydroxyarene, diaminodithiolarene or tetraaminoarene of the type discussed above, and either an aromatic diacid or an aromatic diacid chloride. The biscyclobutarene oligomers prepared by this reaction are bridged by a divalent polybenzoxazole, polybenzothiazole, or polybenzimidazole. For purposes of describing this invention, an aromatic diacid or aromatic diacid chloride includes diacid derivatives such as aromatic dinitriles, diesters, diamides, imidate esters, and alkali and alkaline earth metal salts of the diacid or diacid chloride. For example, an aromatic diester can be prepared by reacting the corresponding diacid or diacid chloride with phenol. For the purposes of this invention, the biscyclobutarene oligomers can also use some AB type benzoxazole, benzothiazole, and benzimidazole monomers such as shown in the formula below:

where Q is either a carboxylic acid or acid halide group (e.g., —COOH or —COCl) or a derivative or precursor thereof.

The required reaction conditions are similar to the conditions described for preparing the monomers of this invention. Preferred biscyclobutarene oligomers are prepared from benzocyclobutene-4-carboxylic acid and have the following formula:

wherein L is a benzoxazole, benzothiazole or benzimidazole linkage of any of the formulae:

wherein

Z is an oxygen or sulfur atom or a $$-\overset{R'}{\underset{|}{N}}-$$

group wherein R' is hydrogen or a monovalent aliphatic or aromatic radical;

R is methyl, halo, phenyl, or phenyloxy;

$R^1$ is a direct bond, arylene, oxygen, carbonyl, sulfur, sulfinyl, or sulfonyl;

m is zero, 1 or 2; and n is zero, 1, 2 or 3;

Ar is arylene, biarylene, or two arylene moieties bridged by oxygen, carbonyl, sulfur, sulfinyl, or sulfonyl; and p is either zero or an integer of 1 or more, preferably either zero or an integer between 1 and 1,000, inclusive.

Preferred arylene is phenylene; preferred oligomers are depicted when Ar in the formula is phenylene, biphenylene, and two phenylene moieties bridged by oxygen, carbonyl, sulfur, sulfinyl, or sulfonyl. The preferred L linkage is a bisbenzoxazole linkage corresponding to the following formula:

More preferred biscyclobutarene oligomers are depicted when Ar in the formula is either biphenylene or two phenylene moieties bridged by oxygen or carbonyl. The most preferred biscyclobutarene oligomer is depicted when Ar is biphenylene and the subscript n is zero, and has the following formula:

(II)

The reactive biscyclobutarene oligomers exist as a mixture of oligomers wherein the value of the subscript p for each component of the mixture varies over a wide range. The average value of the subscript p for an oligomer prepared by the method of this invention is determined by the relative proportions of cyclobutarene-carboxylic acid, either diaminodihydroxyarene, diaminodithiolarene, or tetraaminoarene and either aromatic diacid or aromatic diacid chloride employed in the reaction.

In another embodiment of this invention, two or more different diaminodihydroxyarenes or diaminodithiolarenes or tetraaminoarenes are reacted with a cyclobutarene-carboxylic acid and either an aromatic diacid or an aromatic diacid chloride. A reactive biscyclobutarene oligomer having an unsymmetrical divalent bridging member can thus be prepared. A biscyclobutarene having an unsymmetrical bridging member may be easier to process than a biscyclobutarene having a symmetrical bridging member (symmetry may cause crystallization which makes the melting of the monomer or oligomer more difficult). Similar results may be obtained using two or more aromatic diacids or aromatic diacid chlorides.

The biscyclobutarene monomers and reactive oligomers of this invention can be subjected to ring scission polymerization conditions to prepare highly crosslinked, three-dimensional polymeric networks that are thermooxidatively stable at high temperatures for prolonged time periods. In preferred embodiments, the prepared polymers exhibit no more than a 10 weight percent loss after exposure in air at 316° C. for 900 hours, preferably no more than a 10 weight percent loss after exposure in air at 343° C. for 200 hours. In this context, "ring scission polymerization" refers to the reaction of an opened cyclobutane ring on a cyclobutarene moiety with either another opened cyclobutane ring or a moiety capable of reacting with an opened cyclobutane ring.

When the cyclobutane ring of the cyclobutarene moiety opens, it forms a conjugated diene (orthoquinodimethane) that can react with a dienophilic moiety (a "diene loving" moiety). Typically, the opened ring reacts with another opened ring. U.S. Pat. No. 4,540,763 discloses some of the potential reactions that can occur when opened rings react with each other. Also, an opened ring can potentially react with an olefinic or acetylenic moiety via a Diels-Alder reaction as disclosed in Feiser and Feiser, *Organic Chemistry*, 3rd ed., 1980.

The cyclobutane ring of the cyclobutarene moiety can open by subjecting the monomers and reactive oligomers to sufficient heat. Typically, temperatures from about 200° C. to 300° C. are sufficient to open the ring. Polymerization solvents or catalysts are unnecessary, although a copper salt catalyst may lower the required temperature. Gamma radiation and electron beam radiation can also open the ring, but thermal radiation is preferred since it can be applied by conventional methods.

The monomers and oligomers of this invention can be copolymerized with other monomers and reactive oligomers having at least one cyclobutarene-reactive functionality. Advantageously, the comonomer for oligomer chosen will copolymerize with the monomers and oligomers of this invention to form thermooxidatively stable copolymer compositions. Preferred comonomers and oligomers are maleimides, olefins, acetylenes, cyanates, and those having at least one cyclobutarene moiety as described in U.S. Pat. No. 4,540,763 and copending U.S. application Ser. No. 835,013, filed Feb. 28, 1986. An especially preferred comonomer has the following formula:

This comonomer can be prepared by reacting benzocyclobutene-4- carboxylic acid with orthoaminophenol using reaction conditions similar to the conditions necessary for preparing the monomers of this invention described hereinbefore.

The following examples illustrate but do not limit the scope of this invention.

Example 1 - Preparation of a Biscyclobutarene Oligomer With a Divalent Bridging Member Having a Benzoxazole Linkage Benzocyclobutene-4-carboxylic acid ($4.70 \times 10^{-2}$ moles), 4,4'-biphenyldicarboxyl chloride ($2.35 \times 10^{-2}$ moles), 1,3-diamino-4,6-dihydroxybenzene ($4.70 \times 10^{-2}$ moles), 25.0 grams (g) phosphorus pentoxide and 225 g methanesulfonic acid are charged to a 500 milliliter (ml) resin kettle equipped with a magnetic stirring bar and a nitrogen inlet. The mixture is stirred in a nitrogen atmosphere and heated to 100° C. After 3 hours, the reaction mixture is cooled to room temperature and is poured into 1-liter of crushed ice to form a precipitate. The pH of the resulting aqueous slurry is adjusted to a pH of 9 with ammonium hydroxide. The precipitate is collected by filtration, washed thoroughly with water, and dried in a vacuum oven at 90° C. for 8 hours to give the desired product in 95 percent yield.

EXAMPLE 2

Preparation of the Polymer From the Biscyclobutarene Oligomer of Example 1 and the Thermooxidative Stability of the Polymer and Other Polymers A portion of the benzocyclobutene oligomer prepared from Example 1 is placed in a compression mold having a cavity shaped in the form of a disc. The mold is heated to 160° C. and sufficient pressure is applied to make the oligomer flow completely, filling the mold cavity. The mold is then heated under pressure to 270° C. over a period of 3 hours and afterwards is allowed to cool to room temperature while pressure is maintained. After cooling to room temperature, the mold is opened to reveal a solid polymer disc conforming to the shape of the mold cavity. The polymer disc is removed from the mold and is placed in a circulating air oven at 316° C. (600° F.). The disc is removed from the oven at varying times and is weighted to measure the isothermal weight loss of the polymer. After each measurement, the polymer is returned to the oven.

Another portion of the oligomer prepared from Example 1 is similarly polymerized in the compression mold and the resulting polymer is placed in the circulating air oven at 343° C. (650° F.). Again, the polymer disc is removed from the oven at varying times and is weighed to measure the isothermal weight loss.

Figure 1:
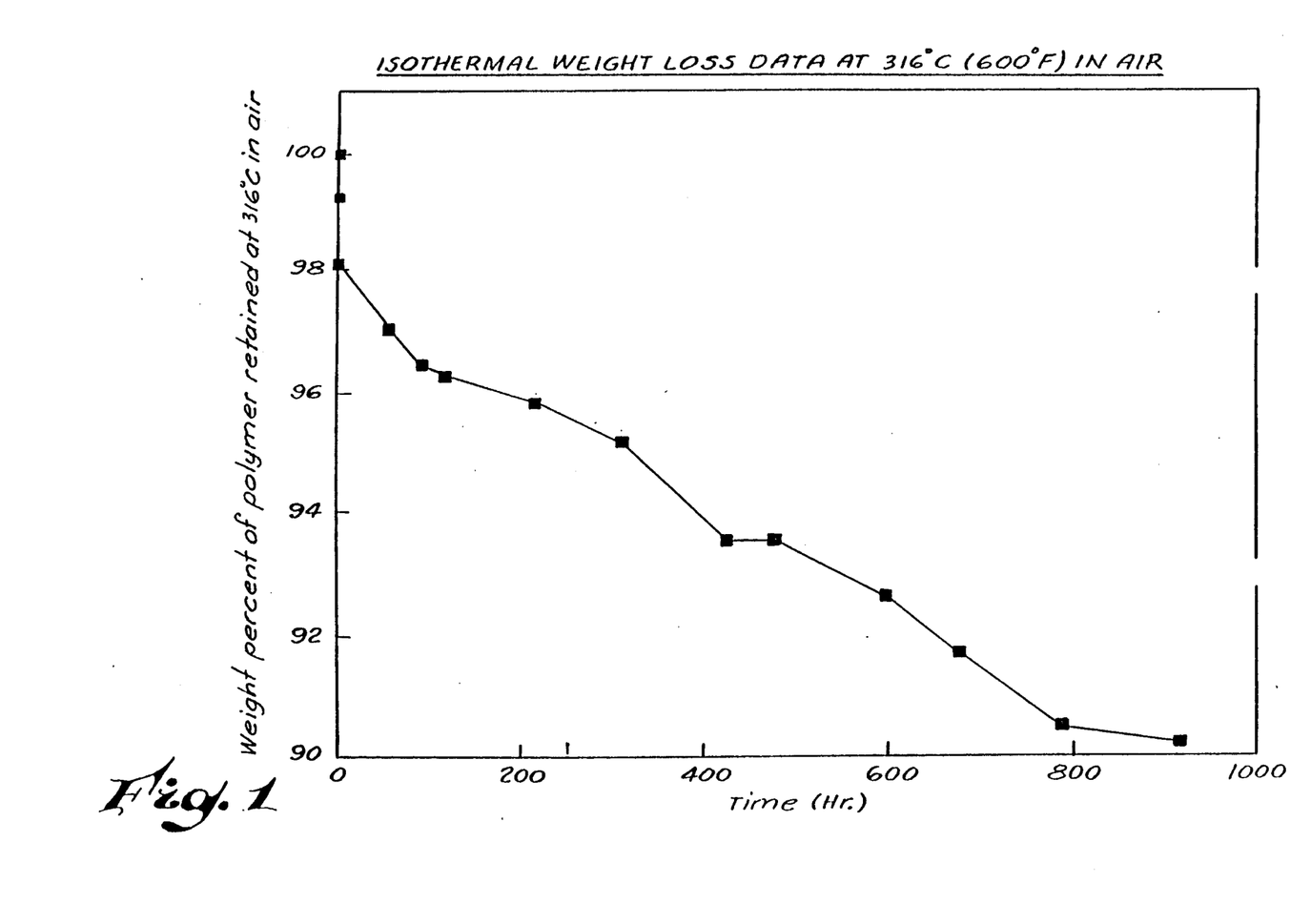
FIGS. 1-4 are graphs of the thermooxidative stability of polymers derived from preferred oligomers of this invention.
Figure 2:
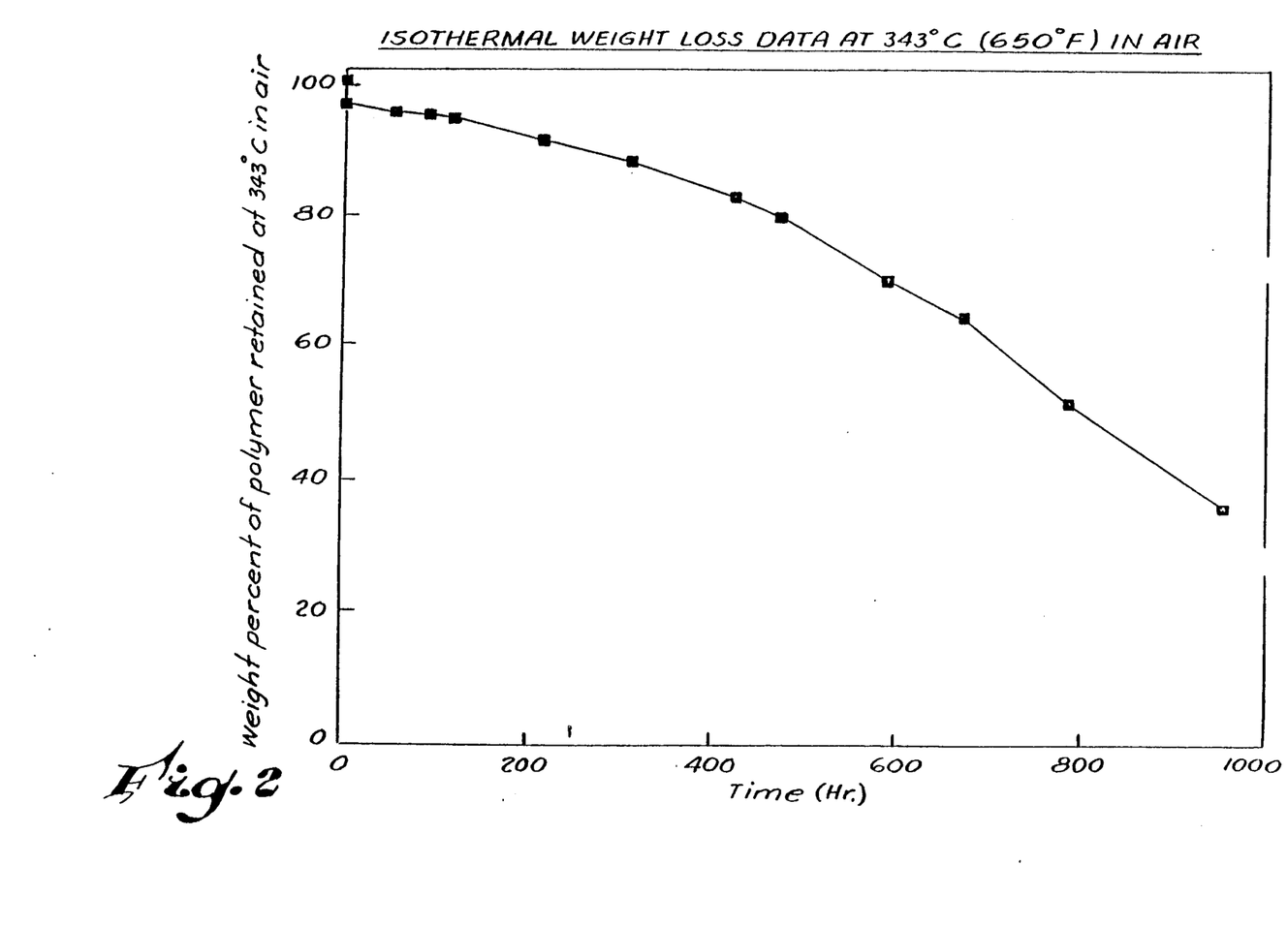

The resulting isothermal weight loss measurements at each temperature are presented in FIGS. 1 and 2.

The results at 316° C. indicate that over 90 percent of the weight of the polymer remains after exposure in air for more than 900 hours. The results at 343° C. indicate that about 90 percent of the weight of the polymer remains after exposure in air for more than 200 hours. These results indicate that a biscyclobutarene oligomer having a divalent bridging member with benzoxazole linkages exhibits outstanding thermooxidative stability at high temperatures for prolonged time periods.

The procedure Example 1 is used to prepare a biscyclobutarene oligomer of the formula:

The biscyclobutarene is polymerized and analyzed for thermooxidative stability at 316° C. and 343° C. using the procedure described in this example. The resulting isothermal weight loss measurements at each temperature are presented in FIGS. 3 and 4.

Figure 3:
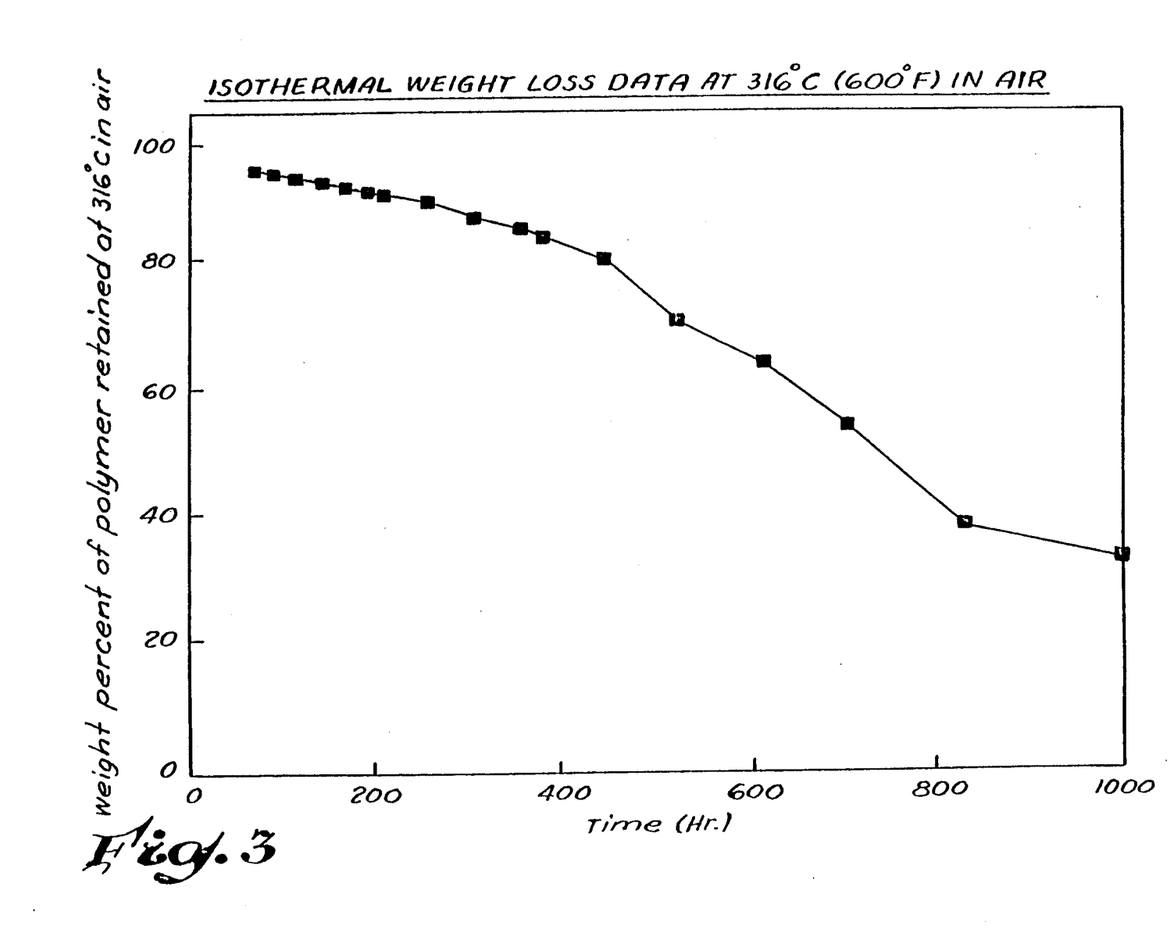
Figure 4:
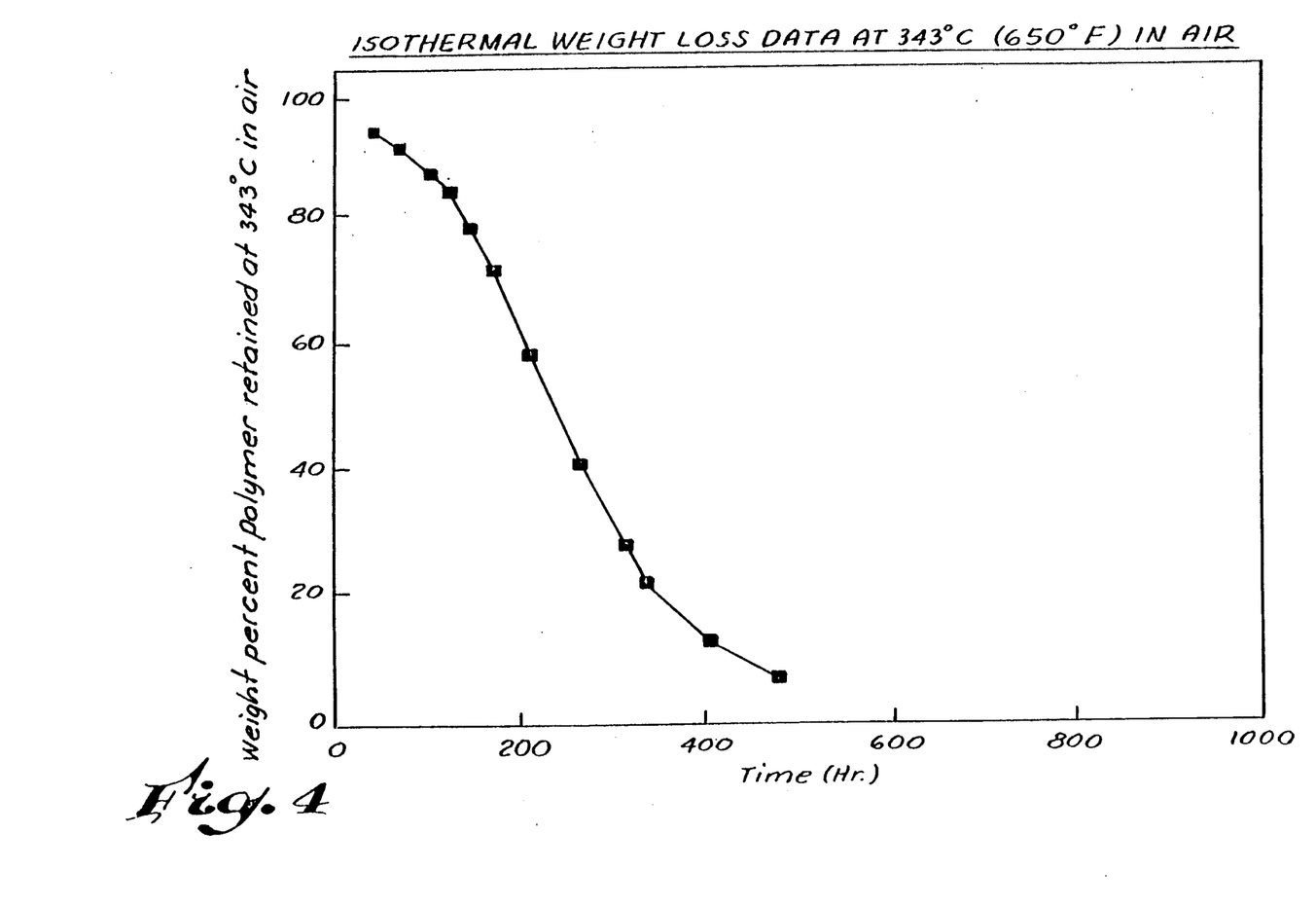

Again, the results at both temperatures indicate outstanding thermooxidative stability at high temperatures for prolonged time periods.

EXAMPLE 3

Preparation of a Bisbenzimidazole-Linked Biscyclobutarene Monomer

In a nitrogen environment, 2.78 parts by wight of 3,3'-diaminobenzidine, 4.32 parts by weight of benzocyclobutene acid chloride and 51.5 parts by weight of polyphosphoric acid are charged to an agitated reaction vessel and are blanketed with nitrogen. The reaction vessel is then sealed and the contents thereof are stirred and permitted to react at a temperature of 95° C. for a time period of 24 hours. At the end of the indicated time period, the contents of the reaction vessel are coagulated in water with a blender to yield a mustard-colored powder which is recovered by filtration and is then reslurried in a blender while neutralizing to a slightly basic pH with NaOH. The resulting product is then collected by filtration, washed twice with water and dried at 80° C. in a vacuum oven.

The resulting product is then subjected to Proton Nuclear Magnetic Resonance Spectroscopy (Proton NMR), Differential Scanning Calorimetry (DSC) and Infrared (IR) Spectroscopy and is determined to correspond to the following structural formula:

EXAMPLE 4

Preparation of Polybenzimidazole Oligomer Endcapped With Benzyocyclobutarene

In a nitrogen environment, 2.57 parts by wight of 3,3'-diaminobenzidine, 2.0 parts by weight of benzocyclobutene acid chloride and 45.2 parts by weight of polyphosphoric acid and 1.77 parts by weight of 4,4'-oxybis(benzoylchloride) are charged to a mechanically agitated reaction vessel and blanketed with nitrogen. The reaction vessel is then sealed and the contents thereof are heated with agitation to a temperature of 95° C. and are maintained under those conditions (i.e., at 95° C. with agitation) for a period of 24 hours. At the end of that time period, the contents of the reaction vessel are coagulated as a yellow powder in water in a blender, washed with water and then with a dilute aqueous NaOH solution. After a final water-wash the resulting product is dried at 60° C. in a vacuum oven to yield an olive-green powder.

The resulting product is confirmed to be a benzocyclobutene endcapped polybenzimidazole oligomer via Proton NMR analysis, IR Spectroscopy and Differential Scanning Calorimetry.

EXAMPLE 5

Preparation of Benzothiazole Endcapped with Benzocyclobutene

Ina nitrogen atmosphere, 2.78 parts by wight of 2,5'-diamino-1,4-dietholbenzene, 3.78 parts by weight of 4-benzocyclobutene acid chloride and 39.4 parts by weight of polyphosphoric acid are charged to an agitated reaction vessel and are blanketed with nitrogen. The reaction vessel is then sealed and the contents are heated to, and maintained at, a temperature of 95° C. with agitation, for a period of 24 hours.

At the end of the indicated time period, the contents of the reaction vessel are recovered as a yellow-green powder in accordance with the procedure set forth in Example 3 above.

Analysis by Proton NMR, Differential Scanning Calorimetry and IR Spectroscopy indicates that the resulting reaction product corresponds to the following structure formula:

Upon repeating the procedures of Examples 1-5 with other oligomers and monomers of this invention, similar outstanding results are obtained.

What is claimed is:

1. A biscyclobutarene monomer comprising two cyclobutarene moieties bridged by a divalent radical comprising at least one benzothiazole or benzimidazole linkage.

2. The biscyclobutarene monomer of claim 1 wherein the benzothiazole or benzimidazole linkage has any one of the formulae:

-continued wherein

Z is a sulfur atom or a group wherein R¹ is hydrogen or a monovalent aliphatic or aromatic radical;

R is methyl, halo, phenyl, or phenyloxy;

R¹ is a direct bond, or R¹ represents arylene, oxygen, carbonyl, sulfur, sulfinyl, or sulfonyl;

m is zero, 1 or 2; and n is zero, 1, 2 or 3.

3. A biscyclobutarene monomer represented by the formula:

4. The biscyclobutarene monomer of claim 1 wherein said benzothiazole or benzimidazole linkage contains benzimidazole.

5. The biscyclobutarene monomer of claim 1 wherein said benzothiazole or benzimidazole linkage contains benzothiazole.

6. The biscyclobutarene monomer of claim 2 wherein Z is a group wherein R' is hydrogen or a monovalent aliphatic or aromatic radical.

7. The biscyclobutarene monomer of claim 2 wherein Z is S.

* * * * *